United States Patent
Hazama et al.

(10) Patent No.: US 12,017,980 B2
(45) Date of Patent: Jun. 25, 2024

(54) MONOFUNCTIONAL PHENOLIC COMPOUND, ACTIVE ESTER RESIN AND METHOD FOR PRODUCING THE SAME, AND THERMOSETTING RESIN COMPOSITION AND CURED PRODUCT THEREOF

(71) Applicant: DIC Corporation, Tokyo (JP)

(72) Inventors: Masaki Hazama, Ichihara (JP); Koji Hayashi, Ichihara (JP)

(73) Assignee: DIC Corporation, Tokyo (JP)

( * ) Notice: Subject to any disclaimer, the term of this patent is extended or adjusted under 35 U.S.C. 154(b) by 684 days.

(21) Appl. No.: 17/276,536

(22) PCT Filed: Sep. 12, 2019

(86) PCT No.: PCT/JP2019/035853
§ 371 (c)(1),
(2) Date: Mar. 16, 2021

(87) PCT Pub. No.: WO2020/059624
PCT Pub. Date: Mar. 26, 2020

(65) Prior Publication Data
US 2022/0033333 A1    Feb. 3, 2022

(30) Foreign Application Priority Data

Sep. 18, 2018   (JP) ................. 2018-173248

(51) Int. Cl.
| | | |
|---|---|---|
| *C07C 69/94* | (2006.01) | |
| *C07C 39/225* | (2006.01) | |
| *C08F 12/24* | (2006.01) | |
| *C08F 12/34* | (2006.01) | |
| *C08F 112/34* | (2006.01) | |
| *C08F 212/32* | (2006.01) | |
| *C08G 63/21* | (2006.01) | |
| *H01L 23/14* | (2006.01) | |

(52) U.S. Cl.
CPC ............ *C07C 39/225* (2013.01); *C07C 69/94* (2013.01); *C08F 12/24* (2013.01); *C08F 12/34* (2013.01); *C08F 112/34* (2013.01); *C08F 212/32* (2013.01); *C08G 63/21* (2013.01); *H01L 23/145* (2013.01)

(58) Field of Classification Search
USPC ......................................................... 528/190
See application file for complete search history.

(56) References Cited

U.S. PATENT DOCUMENTS

| | | |
|---|---|---|
| 2004/0110908 A1 | 6/2004 | Idemura et al. |
| 2016/0137796 A1 | 5/2016 | Wright |
| 2017/0129837 A1 | 5/2017 | Onda |

FOREIGN PATENT DOCUMENTS

| | | |
|---|---|---|
| CN | 101812182 A | 8/2010 |
| JP | 2004-169021 A | 6/2004 |
| JP | 2018-044040 A | 3/2018 |
| JP | 2018-070564 A | 5/2018 |
| WO | 2010/148381 A2 | 12/2010 |
| WO | 2014/170645 A1 | 10/2014 |

OTHER PUBLICATIONS

JP 2015220859A Machine Translation (Year: 2015).*
KR102352506B Machine Translation (Year: 2015).*
Auer, M. et al., "Alternating copolymerization and terpolymerization of vinyl-substituted phenolic antioxidants with propene and carbon monoxide by a palladium(II)-based catalyst: Polyketones containing intramolecular stabilizers", Polymer International, 2004, vol. 53, No. 12, pp. 2015-2019. (cited in the ISR).
Auer, M. et al., "Synthesis of Novel-dl-alpha-Tocopherol-Based and Sterically-Hindered-Phenol-Based Monomers and Their Utilization in Copolymerizations over Metallocene/MAO Catalyst Systems. A Strategy to Remove Concerns about Additive Compatibility and Migration", Macromolecules, 2003, vol. 36, No. 22, pp. 8346-8352. (cited in the ISR).
Daumann L. J. et al., "Asymmetric zinc (II)complexes as functional and structural models for phosphoesterases," Dalton Transactions, 2013, vol. 42, No. 26, pp. 9574-9584. (cited in the ISR).
Narita, M. et al., "Syntheses and Reactions of Optically Active Polymers. I. Syntheses and Polymerizations of N-vinylbenzyl-L-amino Acid Derivatives", Bulletin of the Chemical Society of Japan, 1974, vol. 47, No. 1, pp. 197-201. (cited in the ISR).
International Search Report mailed Dec. 17, 2019, issued for PCT/JP2019/035853.

* cited by examiner

*Primary Examiner* — Terressa Boykin
(74) *Attorney, Agent, or Firm* — Locke Lord LLP; James E. Armstrong, IV; Nicholas J. DiCeglie, Jr.

(57) ABSTRACT

Provided are a monofunctional phenolic compound used for producing an active ester resin capable of forming a cured product having excellent dielectric properties and excellent heat resistance, an active ester resin and a method for producing the active ester resin, and a thermosetting resin composition and a cured product of the thermosetting resin composition. Specifically, provided are a monofunctional phenolic compound including one or more vinylbenzyl groups and an active ester resin including a vinylbenzyl structure attached to a terminal group of the molecular chain and derived from the monofunctional phenolic compound. The vinylbenzyl structure preferably includes a vinylbenzyl-modified aryloxycarbonyl group.

11 Claims, 2 Drawing Sheets

MONOFUNCTIONAL PHENOLIC COMPOUND, ACTIVE ESTER RESIN AND METHOD FOR PRODUCING THE SAME, AND THERMOSETTING RESIN COMPOSITION AND CURED PRODUCT THEREOF

TECHNICAL FIELD

The present invention relates to a monofunctional phenolic compound, an active ester resin and a method for producing the active ester resin, and a thermosetting resin composition and a cured product of the thermosetting resin composition.

BACKGROUND ART

Curable resin compositions, such as an epoxy resin, have been broadly used for producing electronic components, such as semiconductors and multilayer printed circuit boards, since the cured products thereof have excellent heat resistance and an excellent insulating property. Among the electronic components, semiconductor package substrates have been required to have a smaller thickness. Therefore, the warpage of semiconductor package substrates is likely to occur during packaging. In order to reduce the warpage of package substrates, they are required to have high heat resistance.

In addition, the speed and frequency of the signals used in semiconductor package substrates have been increased. Accordingly, the provision of a thermosetting resin composition capable of forming a cured product that produces a sufficiently low dielectric loss tangent while maintaining a sufficiently low dielectric constant upon receiving a high-speed high-frequency signal has been anticipated. As a material capable of achieving a low dielectric constant and a low dielectric loss tangent, a technique in which an active ester compound is used as a curing agent for epoxy resins is known (e.g., see PTL 1). However, a sufficient degree of heat resistance is not achieved, while a low dielectric constant and a low dielectric loss tangent are achieved.

Examples of the other techniques for producing a thermosetting resin composition having a low dielectric constant and a low dielectric loss tangent include a method in which an epoxy resin having a low dielectric constant and a low dielectric loss tangent is added to the thermosetting resin composition; a method in which a cyanate group is introduced to the thermosetting resin composition; and a method in which a polyphenylene ether is added to the thermosetting resin composition. However, it may be difficult to satisfy various requirements such as a low dielectric constant and a low dielectric loss tangent, high heat resistance, reliability, and halogen-free only by using the above methods in combination with one another in a simple manner.

Under the above circumstances, vinylbenzyl-modified active ester resins have been studied as a resin composition capable of forming a cured product having dielectric properties and heat resistance (e.g., see PTLs 2 and 3).

CITATION LIST

Patent Literature

PTL 1: Japanese Unexamined Patent Application Publication No. 2004-169021
PTL 2: Japanese Unexamined Patent Application Publication No. 2018-70564
PTL 3: Japanese Unexamined Patent Application Publication No. 2018-44040

SUMMARY OF INVENTION

Technical Problem

An object of the present invention is to provide a monofunctional phenolic compound used for producing an active ester resin capable of forming a cured product suitable for an application where further high dielectric properties and further high heat resistance are required, an active ester resin and a method for producing the active ester resin, and a thermosetting resin composition including the active ester resin and a cured product of the thermosetting resin composition.

Solution to Problem

The inventor of the present invention conducted extensive studies of a resin composition capable of forming a cured product having excellent dielectric properties and excellent heat resistance and consequently found that using a vinylbenzyl-modified monofunctional phenolic compound in the production of an active ester resin enables the production of an active ester resin including a vinylbenzyl-modified aryloxycarbonyl group attached to a terminal group of the molecule and that a cured product of the active ester resin has higher dielectric properties and higher heat resistance than cured products of the active ester resins known in the related art. Thus, the present invention was made.

Specifically, the present invention relates to the following:

[1] A monofunctional phenolic compound including one or more vinylbenzyl groups.

[2] The monofunctional phenolic compound described in [1], the monofunctional phenolic compound including a structure represented by Formula (1) or (2).

[Chem. 1]

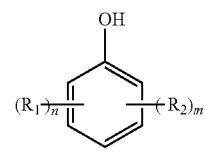

(1)

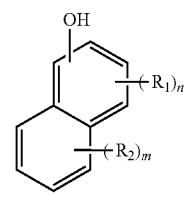

(2)

[wherein, in Formulae (1) and (2), $R_1$ represents a vinylbenzyl group and $R_2$ represents a hydrogen atom, an alkyl group, or an aryl group; in Formula (1), n is an integer of 1 to 5, m is an integer of 0 to 4, and the sum of n and m is 5; in Formula (2), n is an integer of 1 to 7 and m is an integer of 0 to 6; in Formula (2), the sum of n and m is 7; and, in Formulae (1) and (2), $R_1$ may be identical to or different from each other and $R_2$ may be identical to or different from each other]

[3] A raw material composition for producing active ester resins, the raw material composition including the monofunctional phenolic compound described in [1] or [2].

[4] An active ester resin including a vinylbenzyl structure attached to a terminal group of a molecular chain of the active ester resin, the vinylbenzyl structure being derived from the monofunctional phenolic compound described in [1] or [2].

[5] The active ester resin described in [4], wherein the vinylbenzyl structure includes a vinylbenzyl-modified aryloxycarbonyl group.

[6] The active ester resin described in [4] or [5], the active ester resin including vinylbenzyl groups attached to respective terminal groups of a backbone of the active ester resin.

[7] The active ester resin described in any one of [4] to [6], the active ester resin including a structure represented by Formula (I).

[Chem. 2]

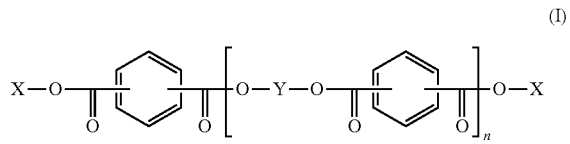

(I)

(wherein, in Formula (I), n represents an integer of 0 to 20, X represents a reaction residue of a monofunctional phenolic compound including a vinylbenzyl group, and Y represents a reaction residue of a polyfunctional phenolic compound)

[8] A method for producing an active ester resin, the method including causing the monofunctional phenolic compound described in [1] or [2] to react with an aromatic polycarboxylic acid.

[9] A thermosetting resin composition including the active ester resin described in any one of [4] to [7] and a curing agent.

[10] The thermosetting resin composition described in [9], the thermosetting resin composition being used for substrates for electronic components.

[11] A cured product of the thermosetting resin composition described in [9] or [10].

[12] A package substrate including the thermosetting resin composition described in [9] or [10].

[13] The package substrate described in [12], the package substrate being a semiconductor package substrate.

Advantageous Effects of Invention

According to the present invention, a monofunctional phenolic compound used for producing an active ester resin capable of forming a cured product having excellent dielectric properties and excellent heat resistance, an active ester resin and a method for producing the active ester resin, and a thermosetting resin composition including the active ester resin and a cured product of the thermosetting resin composition may be provided.

DESCRIPTION OF EMBODIMENTS

Figure 1:
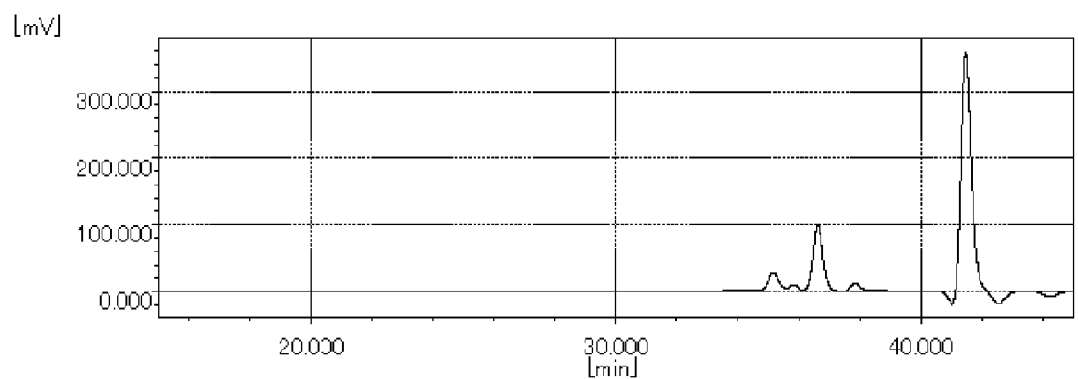
FIG. 1 is a GPC chart of a monofunctional phenolic compound prepared in Example 1.
Figure 2:
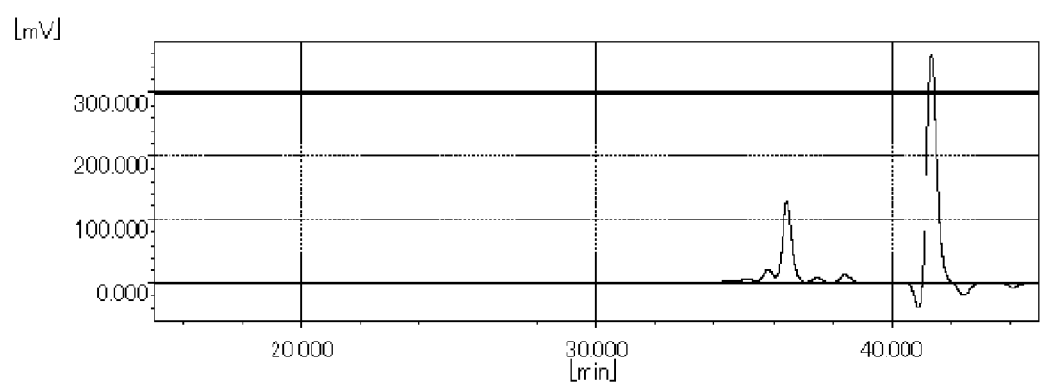
FIG. 2 is a GPC chart of a monofunctional phenolic compound prepared in Example 2.
Figure 3:
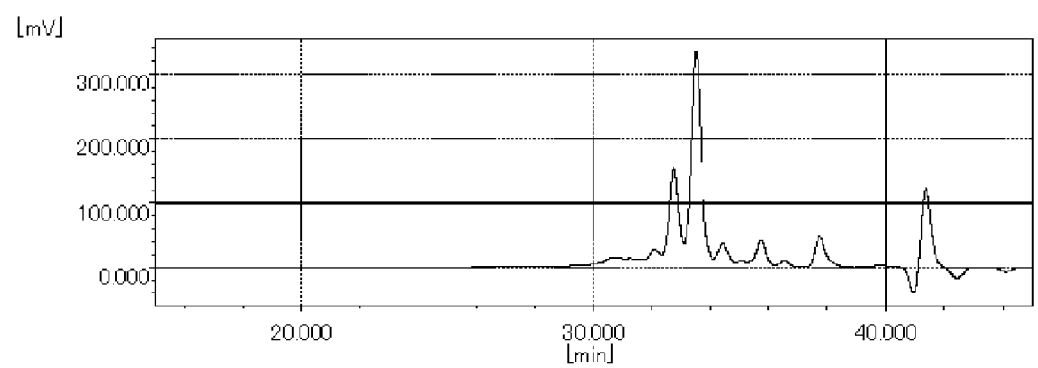
FIG. 3 is a GPC chart of an active ester resin (A-3) prepared in Example 3.
Figure 4:
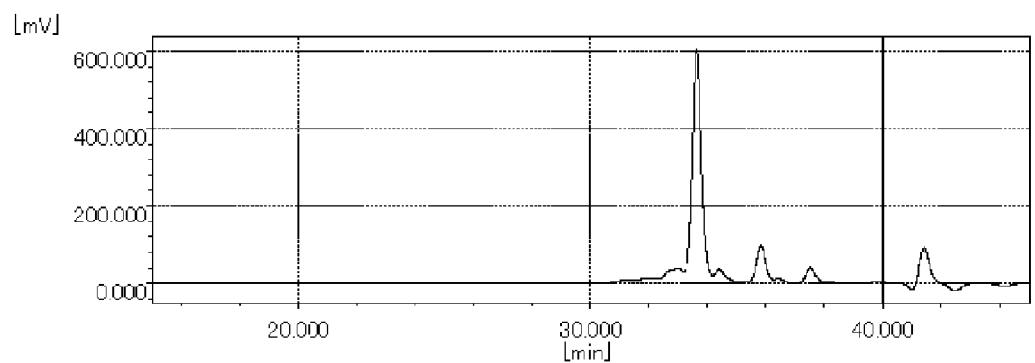
FIG. 4 is a GPC chart of an active ester resin (A-4) prepared in Example 4.

Details of an embodiment of the present invention are described below. The present invention is not limited by the following embodiment. Various modifications may be made without impairing the advantageous effects of the present invention.

[Phenolic Compound]

A phenolic compound according to the embodiment is a monofunctional phenolic compound including one or more vinylbenzyl groups. The vinylbenzyl groups are preferably attached directly to an aromatic ring included in the monofunctional phenolic compound.

The monofunctional phenolic compound may be, for example, one or more selected from monocyclic and polycyclic aromatic compounds including one phenolic hydroxyl group. Examples of the monofunctional phenolic compound include the following aromatic monohydroxy compounds: phenol, o-cresol, m-cresol, p-cresol, 3,5-xylenol, 2,6-xylenol, o-phenylphenol, p-phenylphenol, 2-benzylphenol, 4-benzylphenol, 4-(α-cumyl)phenol, α-naphthol, and β-naphthol. In particular, the use of one or more aromatic monohydroxy compounds selected from α-naphthol, β-naphthol, o-phenylphenol, and p-phenylphenol enables the production of a cured product having excellent heat resistance and a further low dielectric loss tangent.

Examples of the vinylbenzyl group include an ethenylbenzyl group, an isopropenylbenzyl group, and a normal propenylbenzyl group. Among these, an ethenylbenzyl group is preferable in consideration of ease of industrial availability and curability.

The monofunctional phenolic compound may include one or more substituents, such as an alkyl group or an aryl group, in addition to the vinylbenzyl group. Examples of the alkyl group include an alkyl group having 1 to 20 carbon atoms and preferably having 1 to 6 carbon atoms. Examples of the alkyl group having 1 to 6 carbon atoms include a methyl group, an ethyl group, a normal propyl group, an isopropyl group, a normal butyl group, a tertiary butyl group, a pentyl group, a normal hexyl group, and a cyclohexyl group. Examples of the aryl group include a benzyl group, a naphthyl group, and a methoxynaphthyl group.

Specific examples of the monofunctional phenolic compound including a vinylbenzyl group include the monofunctional phenolic compound represented by Formula (1) or (2) below.

[Chem. 3]

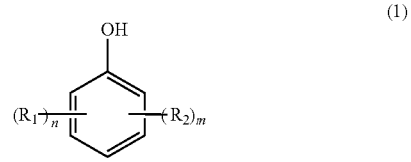

(1)

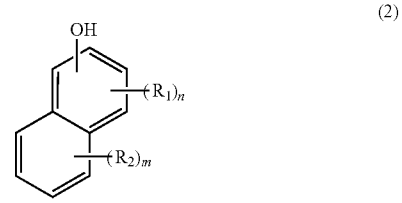

(2)

[in Formulae (1) and (2), $R_1$ represents a vinylbenzyl group and $R_2$ represents a hydrogen atom, an alkyl group, or an aryl group; in Formula (1), n is an integer of 1 to 5, m is an integer of 0 to 4, and the sum of n and m is 5; in Formula (2), n is an integer of 1 to 7 and m is an integer of 0 to 6; in Formula (2), the sum of n and m is 7; and, in Formulae (1) and (2), $R_1$ may be identical to or different from each other and $R_2$ may be identical to or different from each other]

In Formula (2), the hydroxyl group, $R_1$, and $R_2$ may be bonded to any of the rings as a substituent attached to the naphthalene ring.

Examples of the alkyl group include an alkyl group having 1 to 20 carbon atoms and preferably having 1 to 6 carbon atoms. Examples of the alkyl group having 1 to 6 carbon atoms include a methyl group, an ethyl group, a normal propyl group, an isopropyl group, a normal butyl group, a tertiary butyl group, a pentyl group, a normal hexyl group, and a cyclohexyl group. Examples of the aryl group include a phenyl group, a benzyl group, a naphthyl group, and a methoxynaphthyl group.

The monofunctional phenolic compound including a vinylbenzyl group is preferably the compound in which $R_2$ is selected from a hydrogen atom, a methyl group, and an aryl group in order to further enhance the heat resistance and dielectric properties of a cured product of the active ester resin.

Using the monofunctional phenolic compound including one or more vinylbenzyl groups in the production of an active ester resin enables the production of an active ester resin including a vinylbenzyl-modified aryloxycarbonyl group attached to a terminal group of the molecule.

Accordingly, the monofunctional phenolic compound including one or more vinylbenzyl groups may be suitably used as a raw material composition for producing active ester resins. The raw material composition for producing active ester resins may include an aromatic carboxylic acid or halide thereof capable of reacting with the monofunctional phenolic compound to form an ester structure. The aromatic carboxylic acid or halide thereof is preferably an aromatic polycarboxylic acid or halide thereof. The aromatic polycarboxylic acid or halide thereof is described below.

[Method for Producing Monofunctional Phenolic Compound]

The method for producing the monofunctional phenolic compound including a vinylbenzyl group is not limited; for example, a synthesis method in which dehydrohalogenation is performed using an alkali compound, which is known in the related art, may be used. The monofunctional phenolic compound including a vinylbenzyl group may be produced by, for example, dissolving a vinylbenzyl halide, a polyhydric phenolic compound, and a phase-transfer catalyst, such as an ammonium salt, in an organic solvent, such as toluene, methyl isobutyl ketone, or methyl ethyl ketone, adding an alkali compound to the resulting solution, and subsequently stirring the solution while heating it. In particular, a hydrotalcite is preferably used as an alkali compound in order to increase the yield of a compound including a phenolic group and a vinylbenzyl group.

[Active Ester Resin]

An active ester resin according to the embodiment includes a vinylbenzyl structure attached to a terminal group of the molecular chain and preferably includes vinylbenzyl structures attached to the respective terminal groups of the backbone, the vinylbenzyl structures being derived from the above-described monofunctional phenolic compound including a vinylbenzyl group. The vinylbenzyl structure is preferably a vinylbenzyl-modified aryloxycarbonyl group.

The term "active ester resin" used herein refers to a compound or resin including an ester structure derived from a phenolic group and an aromatic carboxylic group.

Examples of the active ester resin include an active resin produced using compounds selected from the monofunctional phenolic compound (a1) including a vinylbenzyl group and an aromatic polycarboxylic acid or halide thereof (a2) as reaction raw materials. The reaction raw materials may include a compound (a3) including two or more phenolic hydroxyl groups and an aromatic monocarboxylic acid or halide thereof (a4) in addition to (a1) and (a2) above.

Since the monofunctional phenolic compound (a1) including a vinylbenzyl group is the same as the above-described monofunctional phenolic compound including one or more vinylbenzyl groups, the description thereof is omitted. The monofunctional phenolic compounds (a1) including a vinylbenzyl group may be used alone or in combination of two or more.

Examples of the aromatic polycarboxylic acid or halide thereof (a2) include aromatic dicarboxylic acids, such as isophthalic acid, terephthalic acid, and 1,4-, 2,3-, or 2,6-naphthalenedicarboxylic acid; aromatic tricarboxylic acids, such as trimesic acid and trimellitic acid; pyromellitic acid; and chlorides of the above acids. The above aromatic polycarboxylic acids and halides thereof may be used alone or in combination of two or more. Among these, isophthalic acid or a mixture of isophthalic acid with terephthalic acid is preferable in consideration of the melting point of the reaction product and in order to enhance solubility in solvents.

The compound (a3) including two or more phenolic hydroxyl groups may be, for example, one or more polyfunctional phenolic compounds selected from monocyclic and polycyclic aromatic compounds including two or more phenolic hydroxyl groups. Examples of the polyfunctional phenolic compounds include the compounds represented by Formulae (3-1) to (3-7) below.

[Chem. 4]

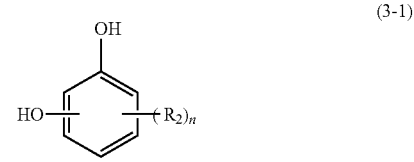

(3-1)

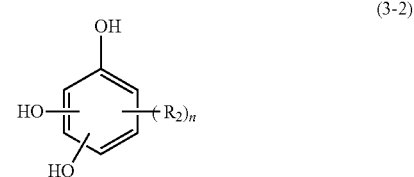

(3-2)

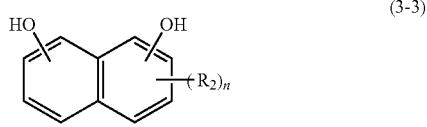

(3-3)

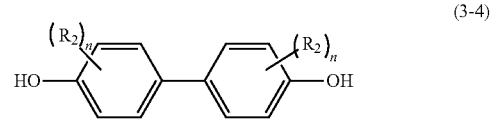

(3-4)

[Chem. 5]

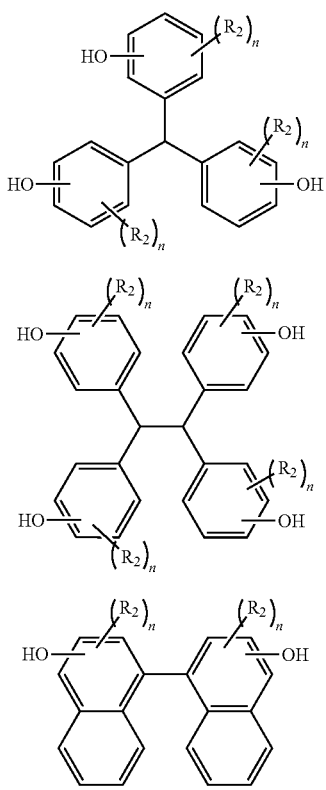

(3-5)

(3-6)

(3-7)

In Formulae (3-1) to (3-7), $R_2$ represents a hydrogen atom, an alkyl group, or an aryl group. In Formulae (3-1), (3-4), (3-5), and (3-6), n is an integer of 0 to 4. In Formula (3-2), n is an integer of 0 to 3. In Formulae (3-3) and (3-7), n is an integer of 0 to 6. The plural $R_2$ groups may be identical to or different from one another. In Formula (3-3), the hydroxyl groups and $R_2$ group may be bonded to any of the rings as a substituent attached to the naphthalene ring. Examples of the alkyl group include an alkyl group having 1 to 20 carbon atoms and preferably having 1 to 6 carbon atoms. Examples of the alkyl group having 1 to 6 carbon atoms include a methyl group, an ethyl group, a normal propyl group, an isopropyl group, a normal butyl group, a tertiary butyl group, a pentyl group, a normal hexyl group, and a cyclohexyl group. Examples of the aryl group include a benzyl group, a naphthyl group, and a methoxynaphthyl group. Examples thereof further include binaphthol.

The polyfunctional phenolic compound may be the compound represented by Formula (4) below.

[Chem. 6]

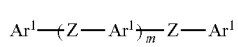

(4)

(in Formula (4), m is an integer of 0 to 20)

In Formula (4) above, $Ar^1$s each independently represent a substituent including a phenolic hydroxyl group; and Zs each independently represent an oxygen atom, a sulfur atom, a ketone group, a sulfonyl group, a substituted or unsubstituted alkylene having 1 to 20 carbon atoms, a substituted or unsubstituted cycloalkylene having 3 to 20 carbon atoms, an arylene having 6 to 20 carbon atoms, or an aralkylene having 8 to 20 carbon atoms.

Examples of the $Ar^1$ groups include, but are not limited to, residues of the aromatic hydroxy compounds represented by Formulae (5-1) and (5-2) below.

[Chem. 7]

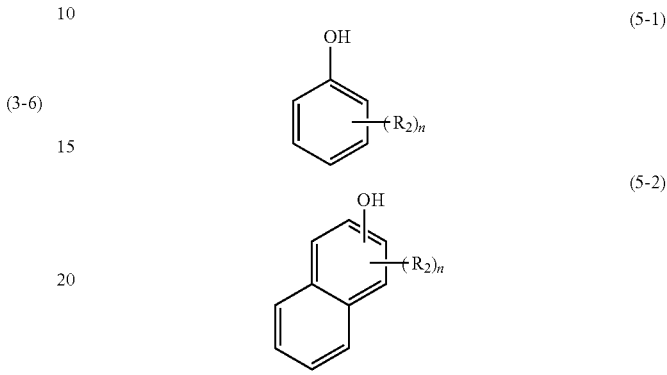

(5-1)

(5-2)

In Formulae (5-1) and (5-2), $R_2$ is any of a hydrogen atom, an alkyl group, and an aryl group. In Formula (5-1), n is an integer of 0 to 5. In Formula (5-2), n is an integer of 0 to 7. In Formula (5-2), the hydroxyl group and $R_2$ may be bonded to any of the rings as a substituent attached to the naphthalene ring. The plural $R_2$ groups may be identical to or different from one another. Examples of the alkyl group include an alkyl group having 1 to 20 carbon atoms and preferably having 1 to 6 carbon atoms. Examples of the alkyl group having 1 to 6 carbon atoms include a methyl group, an ethyl group, a normal propyl group, an isopropyl group, a normal butyl group, a tertiary butyl group, a pentyl group, a normal hexyl group, and a cyclohexyl group. Examples of the aryl group include a benzyl group, a naphthyl group, and a methoxynaphthyl group.

Examples of the alkylene having 1 to 20 carbon atoms which is represented by Z include, but are not limited to, methylene, ethylene, propylene, 1-methylmethylene, 1,1-dimethylmethylene, 1-methylethylene, 1,1-dimethylethylene, 1,2-dimethylethylene, propylene, butylene, 1-methylpropylene, 2-methylpropylene, pentylene, and hexylene.

Examples of the cycloalkylene having 3 to 20 carbon atoms include, but are not limited to, cyclopropylene, cyclobutylene, cyclopentylene, cyclohexylene, cyclopentylene, cycloheptylene, and the cycloalkylenes represented by Formulae (6-1) to (6-4) below.

[Chem. 8]

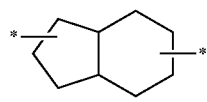

(6-1)

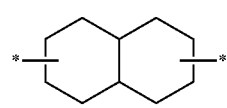

(6-2)

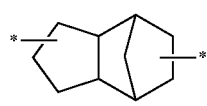

(6-3)

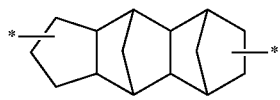 (6-4)

In Formulae (6-1) to (6-4) above, "*" represents the site at which the cycloalkylene is bonded to $Ar^1$.

Examples of the arylene having 6 to 20 carbon atoms include, but are not limited to, the arylene represented by Formula (7-1) below.

[Chem. 9]

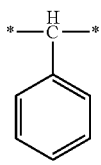 (7-1)

In Formula (7-1) above, "*" represents the site at which the arylene is bonded to $Ar^1$.

Examples of the aralkylene having 8 to 20 carbon atoms include, but are not limited to, the aralkylenes represented by Formulae (8-1) to (8-5) below.

[Chem. 10]

 (8-1)

 (8-2)

 (8-3)

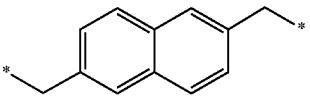 (8-4)

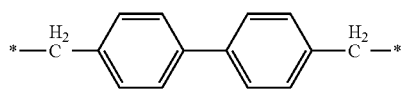 (8-5)

In Formulae (8-1) to (8-5) above, "*" represents the site at which the aralkylene is bonded to $Ar^1$.

Among these, Z in Formula (4) above is preferably the cycloalkylene having 3 to 20 carbon atoms, the arylene having 6 to 20 carbon atoms, or the aralkylene having 8 to 20 carbon atoms and is more preferably the group represented by any of Formulae (6-3), (6-4), (7-1), and (8-1) to (8-5) in consideration of adhesion and dielectric properties. In Formula (4), m is an integer of 0 to 20, is preferably an integer of 0 to 10, is further preferably 0 to 8, and is most preferably 0 to 5 in consideration of solubility in solvents.

The compound (a3) including two or more phenolic hydroxyl groups may include the structure represented by Formula (9) below.

[Chem. 11]

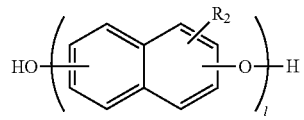 (9)

(In Formula (9), l is an integer of 1 or more, and $R_2$ represents a hydrogen atom, an alkyl group, or an aryl group)

In Formula (9), l is preferably an integer of 1 to 20, is more preferably an integer of 1 to 15, and is further preferably an integer of 1 to 12. Examples of the alkyl group include an alkyl group having 1 to 20 carbon atoms and preferably having 1 to 6 carbon atoms. Examples of the alkyl group having 1 to 6 carbon atoms include a methyl group, an ethyl group, a normal propyl group, an isopropyl group, a normal butyl group, a tertiary butyl group, a pentyl group, a normal hexyl group, and a cyclohexyl group. Examples of the aryl group include a benzyl group, a naphthyl group, and a methoxynaphthyl group.

Among these, the compounds represented by Formulae (4) and (9) are preferable, the compound represented by Formula (4) where $Ar^1$ is a residue of phenol, ortho-cresol, dimethylphenol, phenylphenol, α-naphthol, or β-naphthol and Z is the group represented by any of Formulae (6-3), (7-1), and (8-1) to (8-5) is further preferable, and the compound represented by Formula (9) is more preferable in consideration of the solubility of the reaction product in solvents and the dielectric properties of the reaction product.

Specific examples of the aromatic monocarboxylic acid or halide thereof (a4) include benzoic acid and benzoyl chloride.

Examples of the active ester resin include an active ester resin including the structure represented by Formula (I) below.

[Chem. 12]

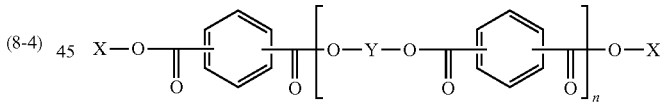 (I)

Specific examples of the active ester resin include the active ester resins represented by Formulae (Ia) and (Ib) below.

[Chem. 13]

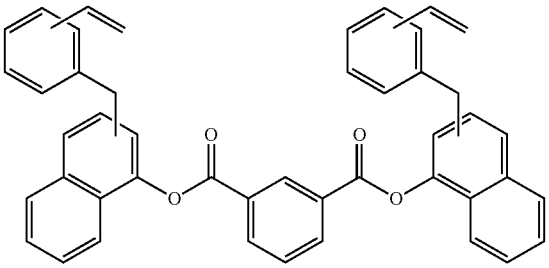 (Ia)

-continued (Ib)

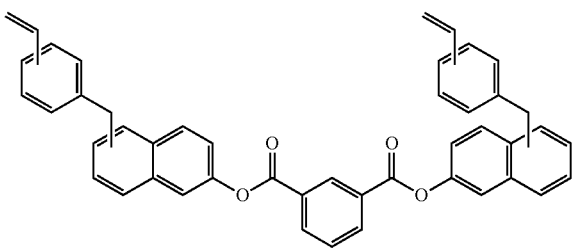

The glass-transition temperature (DSC-Tg) of the active ester resin determined by differential scanning calorimetry (DSC) is preferably, but not limited to, 200° C. or less, is more preferably 150° C. or less, and is further preferably 120° C. or less in consideration of solubility in solvents.

[Method for Producing Active Ester Resin]

A method for producing an active ester resin according to the embodiment includes a step of causing a monofunctional phenolic compound including a vinylbenzyl group to react with an aromatic polyvalent carboxylic acid or derivative thereof (e.g., halide of the acid). The step of causing a monofunctional phenolic compound including a vinylbenzyl group to react with an aromatic polyvalent carboxylic acid or halide thereof is not limited; the active ester resin may be produced by any of the common synthesis methods known in the related art, such as an acetic anhydride method, an interfacial polymerization method, and a solution method. Among these, it is preferable to produce the active ester resin using a halide of the acid, which enables the synthesis of the active ester resin at lower temperatures, in order to prevent gelation from being caused due to the polymerization of the vinylbenzyl group during the synthesis.

[Thermosetting Resin Composition]

A thermosetting resin composition according to the embodiment (hereinafter, referred to simply as "resin composition") includes the above-described active ester resin and a curing agent. The active ester resin is the same as the above-described active ester resin and the description thereof is omitted.

(Curing Agent)

The curing agent may be any compound capable of reacting with the above-described active ester resin; various compounds may be used without any limitation. Examples of the curing agent include a radical polymerization initiator and an epoxy resin. Typical examples of the radical polymerization initiator include an azo compound and an organic peroxide. Among these, in particular, an organic peroxide is preferable because it does not cause a gas to be produced as a by-product. The epoxy resin may be any of the epoxy resins known in the related art. Examples thereof include epoxy resins including two or more epoxy groups, such as glycidyl ether epoxy resins, such as a bisphenol-A epoxy resin, a bisphenol-F epoxy resin, a phenol novolac epoxy resin, a cresol novolac epoxy resin, a biphenyl epoxy resin, a phenol biphenyl aralkyl epoxy resin, a compound produced by epoxidation of an aralkyl resin which includes phenol, naphthol, or the like attached by xylylene bonding, a compound produced by epoxidation of a dicyclopentadiene-modified phenolic resin, a dihydroxynaphthalene epoxy resin, and a triphenolmethane epoxy resin, glycidyl ester epoxy resins, and glycidyl amine epoxy resins. The above epoxy resins may be used alone or in combination of two or more. Among the above epoxy resins, epoxy resins having a high epoxy equivalent weight, such as the phenol biphenyl aralkyl epoxy resin, the compound produced by epoxidation of an aralkyl resin which includes phenol, naphthol, or the like attached by xylylene bonding, and the compound produced by epoxidation of a dicyclopentadiene-modified phenolic resin, are preferably used.

(Amounts Mixed)

The amounts of the active ester resin and the radical polymerization initiator mixed are preferably adjusted such that the amount of time required for curing is adequate to the conditions under which the cured product is formed. In consideration of the properties of the cured product, the amount of the radical polymerization initiator mixed with the active ester resin is preferably more than 0 part by mass and 1 part by mass or less relative to 100 parts by mass of the resin. When the amount of the radical polymerization initiator falls within the above range, the active ester resin may be cured to a sufficient degree. That is, a resin composition capable of forming a cured product having excellent heat resistance and excellent dielectric properties may be readily produced. The mixing ratio between the active ester resin and the epoxy resin is preferably set such that the equivalent weight ratio between the ester groups included in the active ester resin and the epoxy groups included in the epoxy resin falls within the range of 0.5 to 1.5 and is particularly preferably set such that the above equivalent weight ratio falls within the range of 0.8 to 1.2.

(Curing Accelerator)

The resin composition may optionally include a curing accelerator as needed. Examples of the curing accelerator include a phosphorus-based compound, a tertiary amine, imidazole, a metal salt of an organic acid, a Lewis acid, and an amine complex salt. In particular, in the case where the resin composition is used for producing buildup materials or circuit boards, dimethylaminopyridine and imidazole are preferable in order to enhance heat resistance, dielectric properties, soldering resistance, and the like. In particular, in the case where the resin composition is used for producing semiconductor encapsulants, triphenylphosphine, which is a phosphorus-based compound, and 1,8-diazabicyclo-[5.4.0]-undecene (DBU), which is a tertiary amine, are preferable in order to enhance curability, heat resistance, electric characteristics, moisture-resistance reliability, and the like.

(Other Additive Components)

The resin composition may further include another resin component. Examples of the other resin component include vinyl group-containing compounds, such as styrene, acrylic acid, methacrylic acid, and esters thereof, and cyanate ester resins; bismaleimide resins; benzoxazine resins; allyl group-containing resins, such as triallyl isocyanurate; and polyphosphate esters and phosphate ester-carbonate copolymers. The above resin components may be used alone or in combination of two or more.

The mixing proportion of the other resin component is not limited and may be adjusted appropriately in accordance with, for example, the intended properties of the cured product. The content of the other resin component may be, for example, 1% to 50% by mass of the total amount of the resin composition.

The resin composition may optionally include various additives, such as a flame retardant, an inorganic filler, a silane coupling agent, a release agent, a pigment, and an emulsifier, as needed. Examples of the flame retardant include inorganic phosphorus compounds, such as red phosphorus, ammonium phosphate (e.g., monoammonium phosphate, diammonium phosphate, triammonium phosphate, or ammonium polyphosphate), and amide phosphate; organic phosphorus compounds, such as a phosphate ester compound, a phosphonic acid compound, a phosphinic acid compound, a phosphine oxide compound, a phospholan compound, an organic nitrogen-containing phosphorus compound, and a cyclic organic phosphorus compound (e.g., 9,10-dihydro-9-oxa-10-phosphaphenanthrene-10-oxide, 10-(2,5-dihydroxyphenyl)-10H-9-oxa-10-phospha-phenanthrene-10-oxide, or 10-(2,7-dihydroxynaphthyl)-10H-9-oxa-10-phosphaphenanthrene-10-oxide), and derivatives produced by reacting the above organic phosphorus compounds with a compound such as an epoxy resin or a phenolic resin; nitrogen-based flame retardants, such as a triazine compound, a cyanuric acid compound, an isocyanuric acid compound, and phenothiazine; silicone-based flame retardants, such as a silicone oil, a silicone rubber, and a silicone resin; and inorganic flame retardants, such as a metal hydroxide, a metal oxide, a metal carbonate compound, a metal powder, a boron compound, and a low-melting-point glass. In the case where the above flame retardants are used, the content of the flame retardants is preferably 0.1% to 20% by mass of the total amount of the resin composition.

The inorganic filler is used in the case where, for example, the resin composition is used for producing semiconductor encapsulants. Examples of the inorganic filler include fused silica, crystalline silica, alumina, silicon nitride, and aluminum hydroxide. Among these, fused silica is preferable in order to increase the amount of the inorganic filler added to the resin composition. Although the fused silica may be either irregular or spherical, it is preferable to mainly use spherical fused silica in order to increase the amount of the fused silica added to the resin composition and suppress an increase in the melt viscosity of the resin composition. For increasing the amount of the spherical silica added to the resin composition, it is also preferable to adjust the particle size distribution of the spherical silica appropriately. The amount of the silica added to the resin composition is preferably 0.5 to 95 parts by mass relative to 100 parts by mass of the resin component of the resin composition.

The method for producing the resin composition is not limited. The resin composition may be produced by, for example, mixing the above-described components with a stirrer, a three-roll mill, or the like at, for example, 0° C. to 200° C. to prepare a uniform mixture.

[Cured Product]

The resin composition may be cured by being heated to, for example, about 20° C. to about 250° C. and molded into a shape by any of the common thermosetting methods known in the related art.

A cured product of the resin composition according to the embodiment has a heat resistance of 160° C. or more and a low dielectric loss tangent of $3.0 \times 10^{-3}$ or less at 10 GHz. Therefore, the cured product may be preferably used for producing electronic materials, such as semiconductor package substrates.

[Semiconductor Package Substrate, Etc.]

In the case where the resin composition is used for producing substrates, such as a semiconductor package substrate, generally, it is preferable to dilute the resin composition by adding an organic solvent to the resin composition before use. Examples of the organic solvent include methyl ethyl ketone, acetone, dimethylformamide, methyl isobutyl ketone, methoxypropanol, cyclohexanone, methyl cellosolve, ethyl diglycol acetate, and propylene glycol monomethyl ether acetate. The type of the organic solvent and the amount of the organic solvent added to the resin composition may be adjusted appropriately in accordance with the environment in which the resin composition is used. For example, in the case where the resin composition is used for producing semiconductor package substrates, it is preferable to use a polar solvent having a boiling point of 160° C. or less, such as methyl ethyl ketone, acetone, or dimethylformamide. Moreover, the amount of the polar solvent used is preferably set such that the nonvolatile content falls within the range of 40% to 80% by mass.

Examples of the method for producing a semiconductor package substrate with the resin composition include a method in which a reinforcing substrate is impregnated with the resin composition and then cured to form a prepreg. Examples of the reinforcing substrate include paper, glass fabric, glass nonwoven fabric, aramid paper, aramid fabric, glass mat, and glass roving fabric. The amount of the resin composition with which the reinforcing substrate is impregnated is not limited. Generally, it is preferable to adjust the amount of the resin composition used such that the resin content in the prepreg falls within the range of 20% to 80% by mass.

EXAMPLES

The present invention is described more specifically with reference to Examples below, which do not limit the interpretation of the present invention.

Example 1

Into a flask equipped with a thermometer, a dropping funnel, a cooling tube, a fractionating column, and a stirrer, 72.1 g (0.5 moles) of α-naphthol, 156 g of hydrotalcite (KYOWAAD 500SH produced by Kyowa Chemical Industry Co., Ltd.), and 608 g of toluene were charged. Then, the temperature was increased to 70° C. Subsequently, 76.3 g (0.5 moles) of CMS-P (a mixture of meta-chloromethylstyrene with para-chloromethylstyrene, produced by AGC Seimi Chemical Co., Ltd.) was added dropwise to the flask. Then, the temperature was increased to 110° C. After the reaction had been continued for 5 hours, cooling was performed and filtering was then performed to remove insoluble matter. Hereby, a reaction liquid (A-1) was prepared. Analysis of the reaction liquid confirmed that the hydroxyl equivalent weight was 347 g/eq and the nonvolatile content was 15.6%. This confirmed that a compound having the structure represented by Formula (2-1) below was produced.

[Chem. 14]

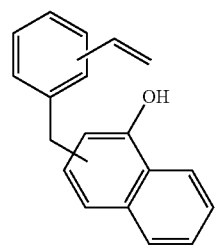

(2-1)

Example 2

Into a flask equipped with a thermometer, a dropping funnel, a cooling tube, a fractionating column, and a stirrer, 72.1 g (0.5 moles) of β-naphthol, 156 g of KYOWAAD 500SH, and 608 g of toluene were charged. Then, the temperature was increased to 70° C. Subsequently, 76.3 g (0.5 moles) of CMS-P was added dropwise to the flask. Then, the temperature was increased to 110° C. After the reaction had been continued for 5 hours, cooling was performed and filtering was then performed to remove insoluble matter. Hereby, a reaction liquid (A-2) was prepared. Analysis of the reaction liquid which was conducted as described above confirmed that the hydroxyl equivalent weight was 352 g/eq and the nonvolatile content was 14.4%. This confirmed that a compound having the structure represented by Formula (2-2) below was produced.

[Chem. 15]

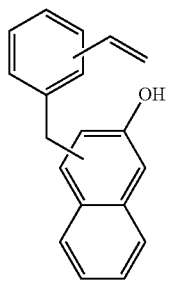

(2-2)

Example 3

Into a flask equipped with a thermometer, a dropping funnel, a cooling tube, a fractionating column, and a stirrer, 445 g of the reaction liquid (A-1) produced in Example 1 and 20.2 g of isophthaloyl chloride were charged. Then, the inside of the system was purged with nitrogen under reduced pressure and a solution was prepared. Subsequently, 0.12 g of tetrabutylammonium bromide was dissolved in the solution. Then, while purging was performed with a nitrogen gas, the temperature of the inside of the system was adjusted to be 60° C. or less and 41.2 g of a 20% aqueous sodium hydroxide solution was added dropwise to the solution over 3 hours. Subsequently, stirring was performed for 1.0 hours under the above conditions. After the reaction had been completed, the solution was left to stand in order to perform liquid separation. The resulting aqueous layer was removed. Water was added to the toluene layer, in which the reaction product was dissolved. Then, the toluene layer was stirred for about 15 minutes and left to stand in order to perform liquid separation. The resulting aqueous layer was removed. The above operation was repeated until the pH of the aqueous layer became 7. Subsequently, drying was performed by heating under reduced pressure. Hereby, an active ester resin (A-3) including the structure represented by Formula (Ia) below was synthesized. No insoluble matter was produced. The Tg of the product was 13° C.; the product was semi-solid. Tg was measured by DSC (measuring device: DSC1 produced by METTLER TOREDO).

[Chem. 16]

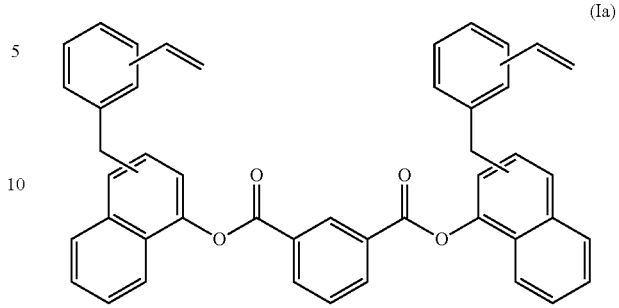

(Ia)

Example 4

Into a flask equipped with a thermometer, a dropping funnel, a cooling tube, a fractionating column, and a stirrer, 733 g of the reaction liquid (A-2) produced in Example 2 and 30.3 g of isophthaloyl chloride were charged. Then, the inside of the system was purged with nitrogen under reduced pressure and a solution was prepared. Subsequently, 0.19 g of tetrabutylammonium bromide was dissolved in the solution. Then, while purging was performed with a nitrogen gas, the temperature of the inside of the system was adjusted to be 60° C. or less and 61.8 g of a 20% aqueous sodium hydroxide solution was added dropwise to the solution over 3 hours. Subsequently, stirring was performed for 1.0 hours under the above conditions. After the reaction had been completed, the solution was left to stand in order to perform liquid separation. The resulting aqueous layer was removed. Water was added to the toluene layer, in which the reaction product was dissolved. Then, the toluene layer was stirred for about 15 minutes and left to stand in order to perform liquid separation. The resulting aqueous layer was removed. The above operation was repeated until the pH of the aqueous layer became 7. Subsequently, drying was performed by heating under reduced pressure. Hereby, an active ester resin (A-4) including the structure represented by Formula (Ib) below was synthesized. No insoluble matter was produced. The Tg of the product, which was measured as described above, was 14° C.; the product was semi-solid.

[Chem. 17]

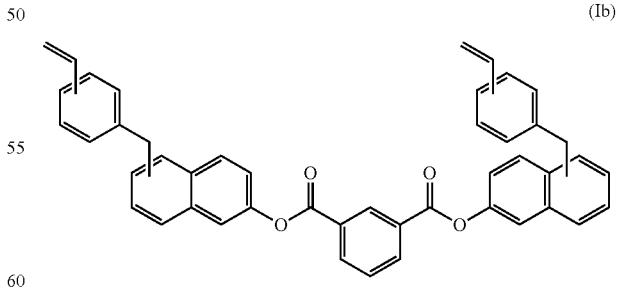

(Ib)

Example 5

Into a flask equipped with a thermometer, a dropping funnel, a cooling tube, and a stirrer, 72.1 g (0.5 moles) of α-naphthol, 76.3 g (0.5 moles) of CMS-P (a mixture of meta-chloromethylstyrene with para-chloromethylstyrene, produced by AGC Seimi Chemical Co., Ltd.), and 148.3 g of toluene were charged. Then, the temperature was increased to 60° C. Subsequently, 150.0 g of a 20% aqueous sodium hydroxide solution (0.75 moles as sodium hydroxide) was added dropwise to the flask. Then, the reaction was continued for 5 hours. After excessive alkali had been neutralized with hydrochloric acid, the resulting solution was left to stand in order to perform liquid separation. The resulting aqueous layer was removed. Water was added to the toluene layer, in which the reaction product was dissolved. Then, the toluene layer was stirred for about 15 minutes and left to stand in order to perform liquid separation. The resulting aqueous layer was removed. Subsequently, dehydration was performed by reducing pressure. Hereby, a reaction liquid (A-5) was prepared. Analysis of the reaction liquid confirmed that the hydroxyl equivalent weight was 295 g/eq and the nonvolatile content was 34.4%. This confirmed that a compound having the structure represented by Formula (2-1) below was produced.

Comparative Synthesis Example 1

Into a flask equipped with a thermometer, a dropping funnel, a cooling tube, fractionating column, and a stirrer, 80.1 g (0.5 moles) of 1,6-dihydroxynaphthalene, 156 g of KYOWAAD 500SH, and 624 g of toluene were charged. Then, the temperature was increased to 70° C. Subsequently, 76.3 g (0.5 moles) of CMS-P was added dropwise to the flask. Then, the temperature was increased to 110° C. After the reaction had been continued for 5 hours, cooling was performed and filtering was then performed to remove insoluble matter. Hereby, a reaction liquid (B-1) was prepared. Analysis of the reaction liquid which was conducted as described above confirmed that the hydroxyl equivalent weight was 177 g/eq and the nonvolatile content was 16.0%. This confirmed that a compound having the structure represented by the following formula was produced.

[Chem. 18]

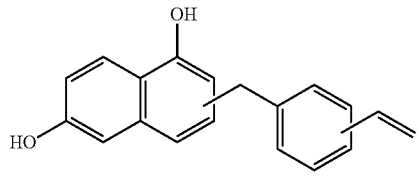

Comparative Example 1

Into a flask equipped with a thermometer, a dropping funnel, a cooling tube, a fractionating column, and a stirrer, 442 g of the reaction liquid (B-1) produced in Comparative synthesis example 1, 57.6 g of α-naphthol, and 80.8 g of isophthaloyl chloride were charged. Then, the inside of the system was purged with nitrogen under reduced pressure and a solution was prepared. Subsequently, 0.27 g of tetrabutylammonium bromide was dissolved in the solution. Then, while purging was performed with a nitrogen gas, the temperature of the inside of the system was adjusted to be 60° C. or less and 164.8 g of a 20% aqueous sodium hydroxide solution was added dropwise to the solution over 3 hours. Subsequently, stirring was performed for 1.0 hours under the above conditions. After the reaction had been completed, the solution was left to stand in order to perform liquid separation. The resulting aqueous layer was removed. Water was added to the toluene layer, in which the reaction product was dissolved. Then, the toluene layer was stirred for about 15 minutes and left to stand in order to perform liquid separation. However, the degree of liquid separation was poor since the bottom layer had been emulsified. The above operation was repeated until the pH of the emulsion layer became 7. Subsequently, drying was performed by heating under reduced pressure. Hereby, an active ester resin (B-2) including the structure represented by Formula (B-2a) below was synthesized. After the synthesis, gelatinous matter insoluble in solvents or water was adhered on the flask. The Tg of the product, which was measured as described above, was 43° C.; the product was solid.

[Chem. 19]

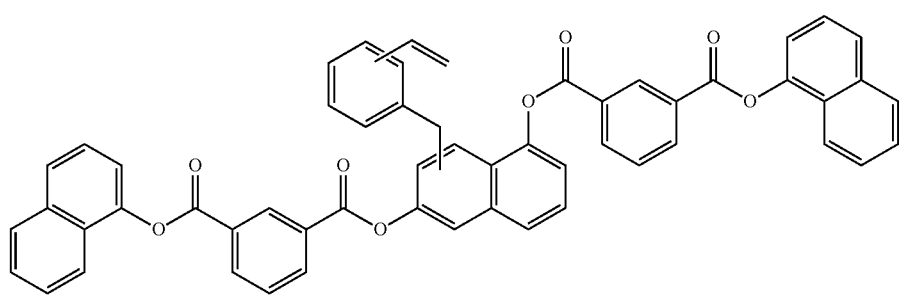

(B-2a)

[Preparation of Resin Composition and Cured Product Thereof]

In Examples 3 and 4 and Comparative example 1, the components were mixed with one another in the specific amounts described in Table 1 to form a curable resin composition, which was poured into a mold having a thickness of 1.6 mm. Subsequently, heating was performed at 120° C. for 120 minutes and then at 180° C. for 60 minutes in order to cure the resin composition. The heat resistance and dielectric loss tangent of the resulting cured product were determined as described below. Table 1 describes the results.

(Heat Resistance)

A piece having a width of 5 mm and a length of 54 mm was taken from the cured product and used as a specimen. The heat resistance of the specimen was determined with a viscoelasticity measuring equipment (DMA: solid viscoelasticity measuring equipment "RSAII" produced by Rheometric, rectangular tension method: frequency: 1 Hz, heating rate: 3° C./min).

(Dielectric Loss Tangent)

The dielectric loss tangent of the specimen at 10 GHz which had been dried in vacuum by heating and then stored in a chamber having a temperature of 23° C. and a humidity of 50% for 24 hours was measured by a resonant cavity method with a network analyzer "E8362C" produced by Agilent Technologies, Inc.

TABLE 1

|  |  | Example 3 | Example 4 | Comparative example 1 |
|---|---|---|---|---|
| Active ester resin (A-3) | mass part | 50 |  |  |
| Active ester resin (A-4) | mass part |  | 50 |  |
| Active ester resin (B-2) | mass part |  |  | 50 |
| Styrene | mass part | 50 | 50 | 50 |
| Dicumyl peroxide | mass part | 1.0 | 1.0 | 1.0 |
| Heat resistance | ° C. | 167 | 164 | 120 |
| Dielectric loss tangent <10 GHz> | — | 0.0026 | 0.0030 | 0.0035 |

As described in Table 1, the cured product formed of the resin composition including the active ester resin prepared in Example 3 had a high heat resistance of 167° C. and a low dielectric loss tangent of $2.6\times10^{-3}$ at 10 GHz. Similarly, the cured product formed of the resin composition including the active ester resin prepared in Example 4 had a high heat resistance of 164° C. and a low dielectric loss tangent of $3.0\times10^{-3}$ at 10 GHz.

In contrast, the cured product formed of the resin composition including the active ester resin prepared in Comparative example 1 had a dielectric loss tangent of $3.5\times10^{-3}$ at 10 GHz and a heat resistance of 120° C.

Thus, the resin compositions including the active ester resin according to the embodiment had higher heat resistance and a lower dielectric loss tangent than the resin composition known in the related art.

The invention claimed is:

1. A monofunctional phenolic compound comprising one or more vinylbenzyl groups, including a structure represented by Formula (1) or (2)

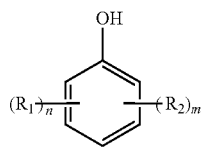

(1)

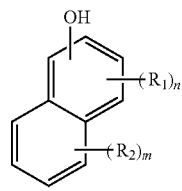

(2)

wherein, in Formulae (1) and (2), $R_1$ represents a vinylbenzyl group and $R_2$ represents a hydrogen atom, an alkyl group, or an aryl group; in Formula (1), n is an integer of 1 to 5, m is an integer of 0 to 4, and the sum of n and m is 5; in Formula (2), n is an integer of 1 to 7 and m is an integer of 0 to 6; in Formula (2), the sum of n and m is 7; and, in Formulae (1) and (2), $R_1$ may be identical to or different from each other and $R_2$ may be identical to or different from each other.

2. A raw material composition for producing active ester resins, the raw material composition comprising the monofunctional phenolic compound according to claim 1.

3. An active ester resin comprising a vinylbenzyl structure attached to a terminal group of a molecular chain of the active ester resin, the vinylbenzyl structure being derived from the monofunctional phenolic compound according to claim 1.

4. A method for producing an active ester resin, the method comprising causing the monofunctional phenolic compound according to claim 1 to react with an aromatic polycarboxylic acid or derivative thereof.

5. The active ester resin according to claim 3, wherein the vinylbenzyl structure includes a vinylbenzyl-modified aryloxycarbonyl group.

6. The active ester resin according to claim 3, the active ester resin including vinylbenzyl groups attached to respective terminal groups of a backbone of the active ester resin.

7. The active ester resin according to claim 3, the active ester resin including a structure represented by Formula (I)

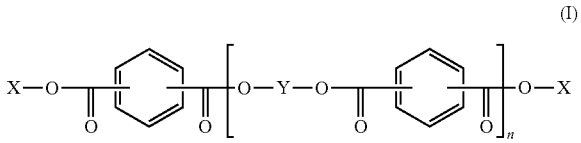

(I)

wherein, in Formula (I), n represents an integer of 0 to 20, X represents a reaction residue of a monofunctional phenolic compound including a vinylbenzyl group, and Y represents a reaction residue of a polyfunctional phenolic compound.

8. A thermosetting resin composition comprising the active ester resin according to claim 3 and a curing agent.

9. The thermosetting resin composition according to claim 8, the thermosetting resin composition being used for substrates for electronic components.

10. A cured product of the thermosetting resin composition according to claim 8.

11. A package substrate comprising the thermosetting resin composition according to claim 8.

* * * * *